(12) United States Patent
Stehr et al.

(10) Patent No.: US 8,540,662 B2
(45) Date of Patent: Sep. 24, 2013

(54) MEDICAL DEVICES HAVING AN ATRAUMATIC DISTAL TIP SEGMENT

(75) Inventors: Richard E. Stehr, Stillwater, MN (US); Martin M. Grasse, Minneapolis, MN (US); Allan M. Fuentes, Mound, MN (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 575 days.

(21) Appl. No.: 12/410,431

(22) Filed: Mar. 24, 2009

(65) Prior Publication Data

US 2010/0249568 A1 Sep. 30, 2010

(51) Int. Cl.
*A61M 3/00* (2006.01)
*A61B 5/04* (2006.01)
*A61M 25/00* (2006.01)
*A61M 37/00* (2006.01)
*A61N 1/00* (2006.01)

(52) U.S. Cl.
USPC .......... 604/41; 600/374; 600/585; 604/95.04; 607/122

(58) Field of Classification Search
USPC .............. 604/95.04, 523–525, 530, 532–534, 604/284; 606/32–41; 607/119–124
See application file for complete search history.

(56) References Cited

U.S. PATENT DOCUMENTS

| | | | |
|---|---|---|---|
| 4,547,193 A * | 10/1985 | Rydell | 604/524 |
| 5,125,895 A | 6/1992 | Buchbinder et al. | |
| 5,171,232 A * | 12/1992 | Castillo et al. | 604/529 |
| 5,342,295 A | 8/1994 | Imran | |
| 5,607,462 A | 3/1997 | Imran | |
| 5,662,606 A * | 9/1997 | Cimino et al. | 604/95.04 |
| 5,683,445 A * | 11/1997 | Swoyer | 607/125 |
| 5,906,605 A | 5/1999 | Coxum | |
| 6,096,036 A * | 8/2000 | Bowe et al. | 606/41 |
| 6,371,955 B1 | 4/2002 | Fuimaono et al. | |
| 6,544,215 B1 * | 4/2003 | Bencini et al. | 604/95.01 |
| 6,569,150 B2 * | 5/2003 | Teague et al. | 604/524 |
| 6,743,227 B2 | 6/2004 | Seraj et al. | |
| 6,752,805 B2 | 6/2004 | Maguire et al. | |
| 7,163,537 B2 * | 1/2007 | Lee et al. | 606/41 |
| 7,371,232 B2 | 5/2008 | Scheib | |
| 2003/0083613 A1 * | 5/2003 | Schaer | 604/95.04 |
| 2005/0222554 A1 | 10/2005 | Wallace et al. | |
| 2006/0095022 A1 | 5/2006 | Moll et al. | |
| 2006/0100610 A1 | 5/2006 | Wallace et al. | |

* cited by examiner

*Primary Examiner* — Linda Dvorak
*Assistant Examiner* — Brian M Antiskay
(74) *Attorney, Agent, or Firm* — Wiley Rein LLP

(57) ABSTRACT

A kit for the diagnosis or treatment of tissue in a body cavity includes an introducer and a catheter insertable through the lumen of the introducer having a proximal segment, a working segment and a flexible distal tip segment. The flexible distal tip segment is located adjacent the distal end of the working segment and includes a proximal end, a distal end and a pre-formed bend or curve that permits the catheter to exit the introducer in a lateral direction relative to the introducer body to prevent inadvertent damage to the tissue during a medical procedure. All or part of the working segment and the flexible distal tip segment may be adhesive-filled. The catheter may also include a plurality of sensing and/or energy delivery elements on the working segment and a shape-memory wire terminating at the distal end of the working segment. Methods of use and methods of manufacturing are also described.

25 Claims, 3 Drawing Sheets

MEDICAL DEVICES HAVING AN ATRAUMATIC DISTAL TIP SEGMENT

BACKGROUND OF THE INVENTION a. Field of the Invention

The present disclosure pertains generally to electrophysiological devices and methods for diagnosing and treating biological tissue and, more particularly, to catheters for diagnosing or treating cardiac tissue having an atraumatic distal tip segment.

b. Background Art

The present disclosure relates to medical devices, such as catheters, employed for diagnostic and/or therapeutic procedures to treat or diagnose biological tissue, more specifically in minimally invasive cardiac electrophysiology studies and/or cardiac ablation procedures. Catheters of the above described type are known in the art including, for example, catheters having a circular or hoop-shaped configuration in a distal portion of the device. Typically, such catheters are insertable through an introducer and adopt a straightened configuration when enclosed within the introducer. Upon exiting the protective sheath, there is a risk that the distal end of the catheter may perforate the heart or cause damage to the endocardial or epicardial tissue. Thus, it is preferable to have an atraumatic tip at the distal end of the catheter to prevent damage to the tissue. In known devices, this has been accomplished using a round or spherical tip electrode. However, a tip electrode is not always desirable and incorporating a tip electrode increases the complexity and expense of manufacturing. In addition, the use of a tip electrode usually requires the inclusion of a safety wire, which crowds the inner diameter of the device and can be especially burdensome to incorporate in small diameter catheters. Other known devices use a ball of epoxy affixed to the distal end of the device, but there is a risk that the ball of epoxy may fall off inside the body if it is not properly adhered to the device. What are needed therefore, are improved devices having atraumatic distal tips to prevent inadvertent damage to the tissue.

BRIEF SUMMARY OF THE INVENTION

It is desirable to be able to provide medical devices having an atraumatic distal tip segment to prevent inadvertent damage to the tissue during a medical procedure.

It is also desirable to provide medical devices without a distal tip electrode that have an atraumatic distal tip segment.

A kit for the diagnosis or treatment of tissue in a body cavity includes an introducer having an introducer body defining a lumen therethrough and an electrophysiology catheter insertable through the lumen of the introducer body. The electrophysiology catheter includes an elongated catheter body defining a lumen therethrough and having a proximal segment and a working segment located distally of the proximal segment. The working segment has a distal end and a generally circular configuration in an unbiased state. The elongated catheter body also includes a flexible distal tip segment adjacent the distal end of the working segment having a proximal end and a distal end, the proximal end and the distal end being off-set from one another by an angle of between about 100 degrees to about 175 degrees via one of a pre-formed bend and a pre-formed curve. The electrophysiology catheter further includes at least one of a cardiac sensing element and an energy delivery element disposed along an outer surface of the working segment and a shape-memory wire extending through the lumen of the catheter body from the proximal segment and terminating at the distal end of the working segment. When the electrophysiology catheter is pushed through the introducer in a distal direction, the flexible distal tip segment exits a distal end of the introducer in a lateral direction relative to a longitudinal direction of the introducer body.

The pre-formed bend may form an angle of about 115 degrees to about 125 degrees. The flexible distal tip segment may have a length dimension of about 5 mm to about 10 mm or less than about 20 mm. The plurality of sensing and/or energy delivery elements may comprise radiofrequency electrodes. In one embodiment, the electrophysiology catheter includes a plurality of sensing elements and/or energy delivery elements, and the energy delivery elements comprise at least one of a plurality of radiofrequency electrodes, a plurality of acoustic transducers, a plurality of optical elements and a plurality of microwave elements.

In another embodiment, the flexible distal tip segment is fabricated of materials that are free of electrically conductive properties. In a further embodiment, a distal end of the shape-memory wire is secured at the distal end of the working segment. The distal end of the shape-memory wire may be embedded in an adhesive, such as a UV-cured adhesive. In another embodiment, the distal end of the flexible distal tip segment includes one of a plug or a seal, and the plug or the seal comprises an adhesive, such as a UV-cured adhesive.

In a further embodiment, the flexible distal tip segment includes an intermediate section between the proximal end and the distal end, a flowable adhesive material fills the distal end and the proximal end, and the intermediate section comprises a substantially hollow section devoid of the flowable adhesive.

The working segment and the flexible distal tip segment may be integrally-formed as a unitary polymeric piece, or the flexible distal tip segment and the working segment may be formed separately and bonded together. In one embodiment, the pre-formed bend and the working segment curve in the same direction. The electrophysiology catheter may be a 3 French catheter.

In a further embodiment, an electrophysiology catheter having an atraumatic tip includes a body defining a lumen, the body comprising a generally straight proximal segment, a flexible distal tip segment having a pre-formed bend and a working segment having a distal end and a generally circular configuration in an unbiased state, the working segment being located between the proximal segment and the flexible distal tip segment. The electrophysiology catheter further includes a plurality of sensing and/or energy delivery elements disposed along the working segment and a shape-memory wire extending through the lumen and terminating at the distal end of the working segment. The pre-formed bend forms an angle of between about 100 degrees to about 175 degrees, and a length of the flexible distal tip segment comprises about ⅙ the length of the working segment or less.

The pre-formed bend may form an angle of about 115 degrees to about 125 degrees, and the length of the flexible distal tip segment may be about ¹⁄₁₀ the length of the working segment or less. In one embodiment, a distal end of the shape-memory wire is secured at the distal end of the working segment. The distal end of the shape-memory wire may be embedded in an adhesive, such as a UV-cured adhesive. In another embodiment, the flexible distal tip segment comprises a proximal end, a distal end and an intermediate section between the proximal end and the distal end, the distal end and the proximal end are adhesive-filled, and the intermediate section is substantially hollow.

The plurality of sensing and/or energy delivery elements may comprise radiofrequency electrodes, or the plurality of sensing and/or energy delivery elements may comprise at least one of radiofrequency electrodes, acoustic transducers, optical elements and microwave elements.

An advantage of the family of catheters according to the several embodiments described and depicted herein is that they have an atraumatic flexible distal tip segment that reduces the likelihood of inadvertently damaging or puncturing tissue during a medical procedure.

The foregoing and other aspects, features, details, utilities, and advantages of the present invention will be apparent from reading the following description and claims, and from reviewing the accompanying drawings.

DETAILED DESCRIPTION OF THE INVENTION

The present invention provides a family of catheters suitable for use in the human vasculature for known medical procedures, such as cardiac mapping and ablation. For purposes of this description, certain embodiments will be described in connection with an electrophysiology catheter having a circular or helical shaped working segment, which will also be referred to herein as a hoop catheter. It is contemplated, however, that the described features and methods may be incorporated into any number of devices (including catheters having straight or curved configurations, steerable catheters, electrophysiology probes, and the like) as would be appreciated by one of ordinary skill in the art.

Figure 1:
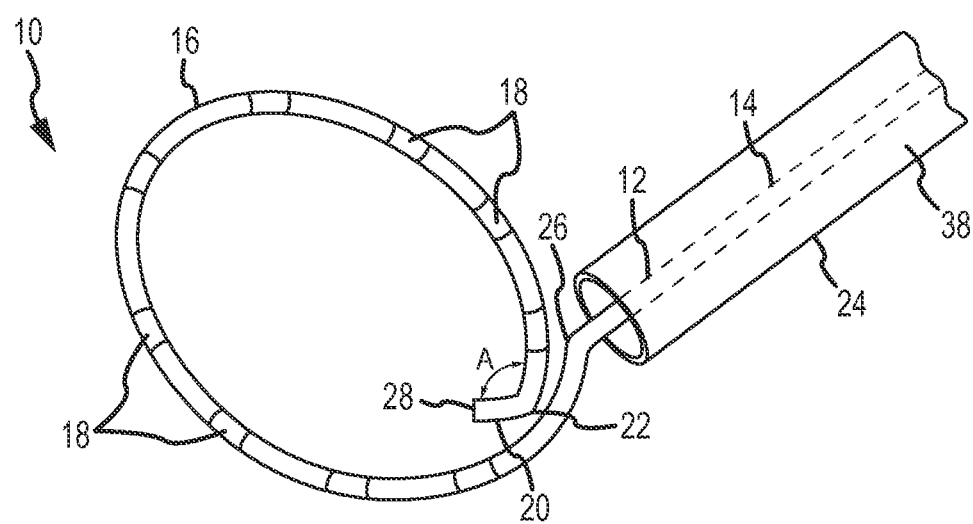
FIG. 1 is a fragmentary, perspective view of a catheter having a flexible distal tip segment within an introducer according to one embodiment of the present invention.
Figure 2:
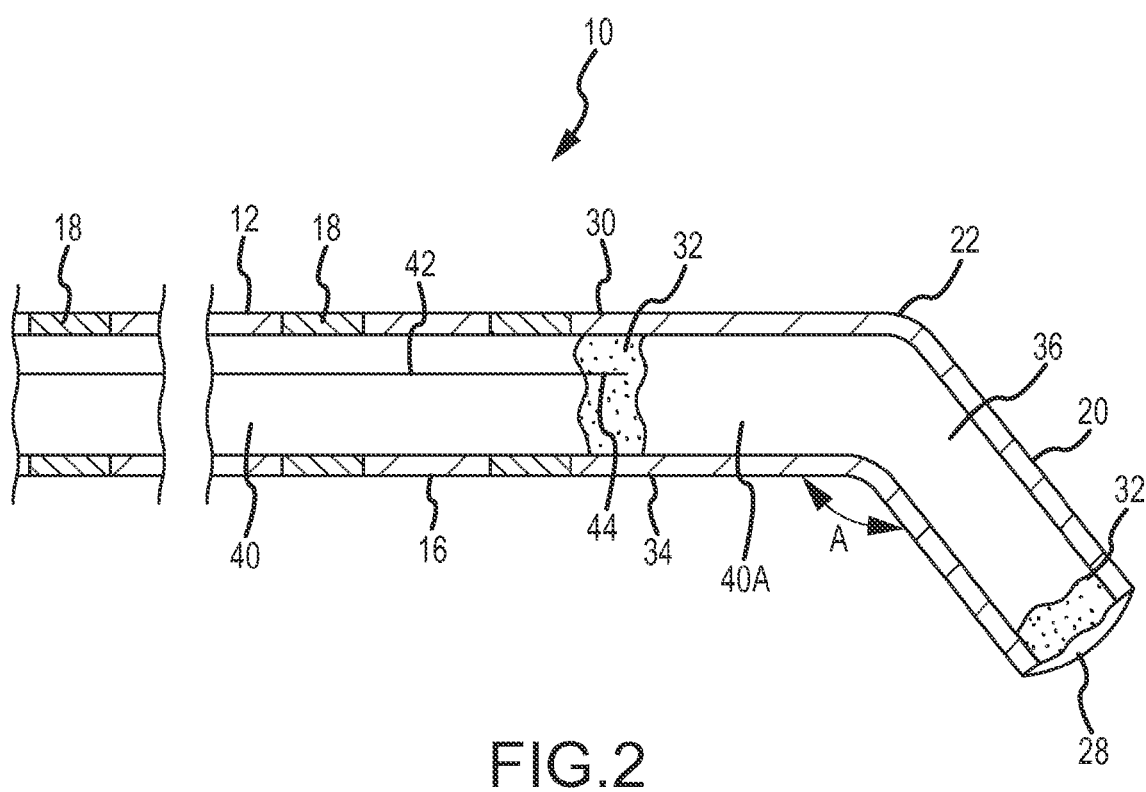
FIG. 2 depicts a cross-sectional view of the catheter shown in FIG. 1.

Referring now to FIGS. 1 and 2, a catheter according to one embodiment of the invention is shown. The catheter 10 has a catheter body 12 having at least one lumen 40 extending therethrough. The catheter body 12 includes a generally straight proximal segment 14, a working segment 16 located adjacent to and distally of the proximal segment 14, and a flexible distal tip segment 20 located adjacent to and distally of the working segment 16. As depicted in FIG. 1, the working segment 16 is located between the proximal segment 14 and the flexible distal tip segment 20. The proximal segment 14 may be connected or secured at its proximal end to a handle or actuator (not shown). As shown in FIG. 1, the catheter 10 may be insertable through an introducer 24 having a lumen 38 extending therethrough.

The flexible distal tip segment 20 includes a pre-formed bend or curve 22 that forms an angle A. In other words, a proximal end 34 and a distal end 28 of the flexible distal tip segment 20 are off-set from one another by angle A via the pre-formed bend 22. The angle A may be about 100 degrees to about 175 degrees. In one embodiment, the angle A is about 115 degrees to about 125 degrees. In another embodiment, the length of the flexible distal tip segment 20 is about 1/6 to about 1/10 the length of the working segment (the length of the working segment being measured in a straightened state). In a further embodiment, the length of the flexible distal tip segment 20 is about 5 mm to about 10 mm, or about 20 mm. However, a person of skill in the art will recognize that the length of the flexible distal tip segment can be adjusted to be less than 5 mm or greater than 20 mm without departing from the scope of the disclosure.

The pre-formed bend 22 permits the flexible distal tip segment 20 to exit the introducer 24 in a lateral direction relative to the longitudinal axis of the introducer 24. For example, with reference to FIG. 3A, as the catheter 10 is advanced through the introducer 24, the distal end 28 of the flexible distal tip segment 20 is directed laterally or sideways through the end of the introducer 24. The flexible distal tip segment 20 prevents the catheter 10 from emerging from the end of the introducer 24 in a straight or direct manner, which decreases the risk that the distal end of the catheter will directly contact the tissue and inadvertently cause damage. Thus, the flexible distal tip segment 20, having an atraumatic structure as described herein, advantageously reduces the likelihood of damaging or puncturing tissue or other structures upon insertion of the catheter 10 into a body cavity. The distal end 28 of the flexible distal tip segment 20 is preferably blunt or rounded.

Flexible distal tip segments 20 may be used with catheters of various dimensions, however, it is particularly useful to incorporate a flexible distal tip segment 20 in catheters having small diameters. The distal end of a small-diameter catheter is more likely to puncture tissue or cause damage after inadvertently coming into contact with a tissue or other internal structure compared to a larger diameter catheter. Thus, it is advantageous to include a flexible distal tip segment 20 having a pre-formed bend 22 on the distal end of a small diameter catheter, for example a 3 French-, 4 French-, or 5 French-sized catheter (having diameters of 1.00 mm, 1.35 mm, and 1.67 mm, respectively). However, as a person of skill in the art will appreciate, a flexible distal tip segment 20 having a pre-formed bend 22 can be incorporated into any size catheter, including catheters greater than 5 French without departing from the scope of the disclosure.

In one embodiment, the working segment 16 has a generally circular or helical configuration in an unbiased state. In other words, in the absence of an applied force the working segment 16 naturally adopts a generally circular or helical shape. Referring to FIG. 2, in one embodiment, a shape-memory wire 42 extends through the lumen 40 of the catheter body 12 and terminates at the distal end 30 of the working segment 16. The shape-memory wire 42 allows the working segment 16 to be straightened from the generally circular or helical configuration upon the application of force, for example, so that the catheter 10 may be inserted through the introducer 24. Once the force is removed, i.e., the working segment 16 is no longer constrained within the introducer, the working segment 16 returns to its original, unbiased, generally circular or helical shape. The shape-memory wire 42 may be made of a nickel-titanium alloy such as Nitinol. The distal end 44 of the shape-memory wire 42 is secured at the distal end 30 of the working segment 16 and preferably does not extend through the lumen 40A of the flexible distal tip segment 16. In one embodiment, the distal end 44 of the shape-memory wire 42 is secured at the distal end 30 of the working segment 16 using an adhesive material 32. The adhesive material 32 may be a UV-cured adhesive, such as a UV-cured epoxy, or any other suitable adhesive material as is known in the art.

In another embodiment, an adhesive material 32 may also be incorporated throughout the working segment 16 and the flexible distal tip segment 20. When incorporated within the working segment 16, the adhesive material 32 inhibits fluid ingress into the lumen of the working segment 16 and prevents electrical noise between the sensing and/or energy delivery elements 18. In this embodiment, a natural or transparent material may be used to form the working segment 16 and the flexible distal tip segment 20, for example natural PEBAX®, so that a UV-cured adhesive can be cured through the working segment 16 and the flexible distal tip segment 20. In one embodiment, the flexible distal tip segment 20 is entirely adhesive-filled. In another embodiment, the flexible distal tip segment 20 is partially hollow. In this embodiment, the distal end 28 of the flexible distal tip segment 20 may include an adhesive material 32 to form a plug or seal to prevent fluid ingress into the lumen 40A, and an intermediate portion 36 of the flexible distal tip segment 20, located between the proximal end 34 and the distal end 28 of the flexible distal tip segment 20, does not contain any adhesive material 32 or other filler (see FIG. 2). Omitting the adhesive material 32 from the intermediate portion 36 of the flexible distal tip segment 20, and in particular the portion comprising the pre-formed bend 22, may provide even greater flexibility.

Figure 3A:
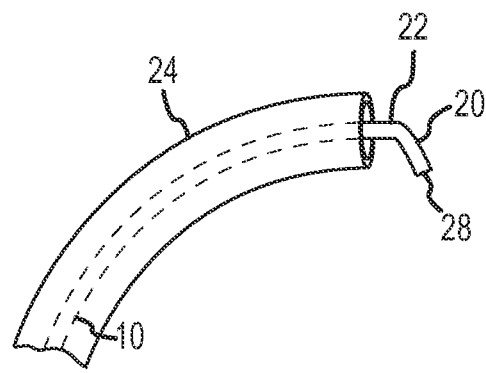
FIGS. 3A-3C schematically illustrate the catheter depicted in FIG. 1 exiting the introducer.
Figure 3B:
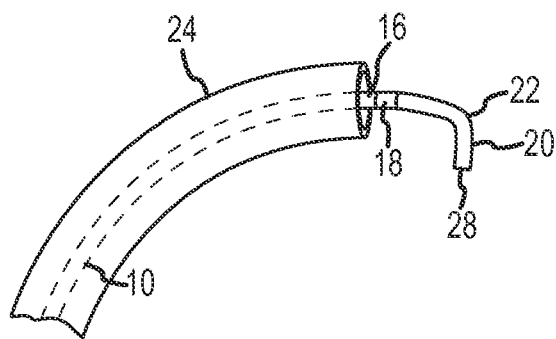
Figure 3C:
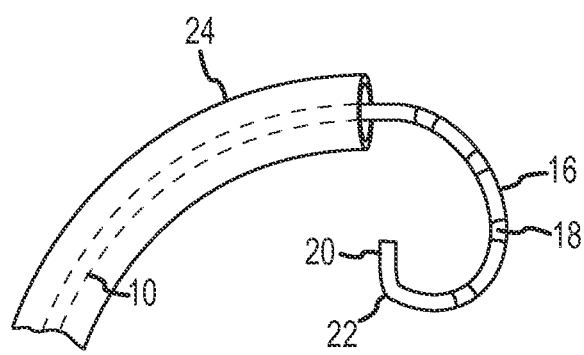

Referring to FIGS. 1 and 3C, as the catheter 10 is advanced through the introducer 24, the working segment 16 exits the introducer 24 and adopts its original generally circular or helical configuration. In one embodiment, the pre-formed bend 22 of the flexible distal tip segment 20 bends in the same direction that the generally circular or helical working segment 16 curves. In this embodiment, the flexible distal tip segment 20 can be viewed as a flexible extension of the working segment 16. Accordingly, the flexible distal tip segment 20 does not interfere with the normal functioning of the catheter 10.

In another embodiment, the working segment 16 has a generally straight configuration in an unbiased state, and the catheter 10 is steerable to form a working segment 16 having a generally circular, helical or curved configuration. In this embodiment, the catheter 10 may include one or more steering elements, such as pull wires or tension-compression members (not shown). The steering elements may extend through the lumen 40 of the catheter body 12 and terminate at or proximal to the distal end 30 of the working segment 16.

The working segment 16 may further include a plurality of cardiac sensing and/or energy delivery elements 18. The sensing and/or energy delivery elements 18 may be radiofrequency (RF) electrodes, ultrasound or other acoustic transducers, optical elements, microwave elements, or a combination thereof. For example, the sensing and/or energy delivery elements 18 may be ring electrodes that can measure impedance and voltage and/or deliver (RF) energy. The embodiment depicted in FIG. 1 shows ten electrodes spaced about the working segment 16. As a person of skill in the art will appreciate, however, any number and combination of sensing and/or energy delivery elements and configurations may be used without departing from the scope of the disclosure. For example, the working segment 16 may include only cardiac sensing elements, only energy delivery elements, or a combination of cardiac sensing and energy delivery elements. Moreover, the same electrodes may be used for both cardiac sensing, pacing and/or ablating. In one embodiment, the working segment 16 may include a plurality of electrodes in which one or more of the electrodes may be used to send a pacing signal and the other electrodes may sense the signal. Any of the electrodes may then be used to ablate the tissue.

Electrical leads (not shown) may extend through the lumen 40, through one or more side lumens (not shown) or may be embedded in a sidewall of the catheter body 12 and coupled to the sensing and/or energy delivery elements 18. A person of skill in the art will appreciate that there are numerous ways to incorporate electrical leads into the catheter body without departing from the scope of the disclosure.

In another embodiment, the flexible distal tip segment 20 is non-conductive or contains no sensing and/or energy delivery elements. In other words, the flexible distal tip segment 20 is fabricated of materials that are free of electrically conductive properties, and/or the flexible distal tip segment 20 does not include a tip electrode. Several advantages of providing a hoop catheter having a flexible distal tip segment 20 in lieu of a tip electrode are simplifying the manufacturing process, reducing the cost of manufacturing and eliminating unnecessary elements from the inner diameter of the catheter, such as safety wires.

The catheter body 12 is flexible and may be made of any suitable material. The catheter body 12 may have an outer polymeric layer or casing made of a polyether block amide, for example, PEBAX®. One of ordinary skill will appreciate that the outer polymeric layer of the catheter body 12 may also be made of other melt processable thermoplastic elastomers with sufficiently high mechanical strength and rigidity, including, without limitation, nylon (for example, Nylon 911), polyamide-based thermoplastic elastomers, polyester-based thermoplastic elastomers (e.g., HYTREL®), thermoplastic polyurethanes (e.g., PELLETHANE®, ESTANE®), and the like, and any combinations thereof. The outer polymeric layer of the catheter body 12 may also be made of an extruded polytetrafluoroethylene (PTFE) tubing (e.g., TEFLON® brand tubing) and other melt-processable fluoropolymers, including, without limitation, fluorinated ethylene-propylene copolymer (FEP), perfluoroalkoxyethylene (PFA), poly(vinylidene fluoride), poly(ethylene-co-tetrafluoroethylene), and the like. Liquid crystal polymers (LCPs) are also suitable materials for the catheter body 12. The catheter body 12 may further include a braided mesh layer and one or more inner polymeric layers.

In one embodiment, the working segment 16 and the flexible distal tip segment 20 may be integrally-formed as a unitary polymeric piece. In other words, the working segment 16 and the flexible distal tip segment 20 may be extruded or otherwise formed from a polymeric material such that there are no seams between the segments. The working segment 16 and the flexible distal tip segment 20 may then be joined to the proximal segment, for example, via a thermal bonding process or using an adhesive or epoxy. In another embodiment, the working segment 16 and the flexible distal tip segment 20 may be separately formed and subsequently secured or fixed together using known methods. The proximal segment 14, the working segment 16 and the flexible distal tip segment may be made of the same material or different materials, such as the materials described herein.

In another embodiment, the catheter body 12 includes a pre-formed transition bend 26 at the point where the proximal segment 14 and the working segment 16 meet. The pre-formed transition bend 26 may form an angle of about 45 degrees to about 90 degrees relative to the longitudinal axis of the proximal segment 14. When it is not constrained within the introducer 24, the pre-formed transition bend 26 causes catheter body 12 to bend where the proximal segment 14 and the working segment 16 meet. This configuration permits better placement of the catheter within a body cavity, for example the ostium of the pulmonary veins.

Methods of diagnosing or treating tissue will now be described with reference to FIGS. 3A-3C. While the methods will be described with respect to cardiac tissue, it should be understood that the methods of the present disclosure can be equally applied to other tissues within the body. An introducer 24 is inserted into a patient and advanced to a location adjacent a tissue to be diagnosed or treated, for example an endocardial or epicardial tissue surface. Then a catheter 10, which may be an electrophysiology catheter, is provided. In one embodiment, the catheter 10 includes an elongated catheter body 12 having a lumen 40 extending therethrough. The catheter body 12 includes a proximal segment 14, a flexible distal tip segment 20 having a pre-formed bend 22 forming an angle of about 100 degrees to about 175 degrees, and a working segment 16 having a distal end 30 and a generally circular configuration in an unbiased state. The working segment 16 is positioned between the proximal segment 12 and the flexible distal tip segment 20. The catheter 10 may also include a plurality of sensing and/or energy delivery elements 18 disposed along an outer surface of the working segment and a shape-memory wire 42 extending through the lumen 40 of the catheter body 12 and terminating at the distal end 30 of the working segment 16.

The catheter 10 is advanced through the introducer 24 until the flexible distal tip segment 20 is exposed at the distal end of the introducer 24 (FIG. 3A). The flexible distal tip segment 20 exits or emerges from the distal end of the introducer 24 in a lateral direction relative to a longitudinal direction of the introducer 24. In other words, because the flexible distal tip segment 20 includes a pre-formed bend 22, the distal end 28 of the flexible distal tip segment 20 emerges in a sideways or oblique direction with respect to a longitudinal axis of the introducer 24. This prevents direct contact of the distal end 28 of the flexible distal tip segment 20 with the tissue and reduces the likelihood of inadvertently damaging or puncturing the tissue when the catheter 10 exits the introducer 24. As the catheter 10 is further advanced through the lumen 38 of the introducer 24, the working segment 16 exits or emerges from the distal end of the introducer 24 and adopts a generally circular or helical configuration (FIG. 3B-3C). The working segment 16 is then placed against the tissue to be diagnosed or treated and the sensing and/or energy delivery elements 18 are used to sense electrical activity to diagnose the tissue and/or deliver energy to treat the tissue. For example, the sensing and/or energy delivery elements 18 may be RF electrodes that are used to ablate tissue or to map a cardiac tissue surface.

A method of manufacturing a catheter according to the present disclosure includes extruding a catheter body 12, the catheter body having a proximal segment 14, a working segment 16 and a flexible distal tip segment 20 and forming a bend 22 in the flexible distal tip segment 20 having an angle "A" (FIG. 2) of between about 100 degrees to about 175 degrees. The bend 22 may be formed during a thermal setting process. For example, the flexible distal tip segment 20 may be heated, placed in a forming fixture, and then cooled to form a desired angle. Alternatively, the flexible distal tip segment 20 may be formed separately from the working segment 16 and bonded or otherwise affixed to the working segment 16. For example, the flexible distal tip segment 20 may be bonded to the working segment 16 using an adhesive, such as an epoxy or a UV-cured epoxy.

A shape-memory wire 42 is inserted through the lumen 40 of the catheter body 12 and secured or otherwise affixed at the distal end 30 of the working segment 16. In one embodiment, the shape-memory wire 42 is embedded in an adhesive at the distal end 30 of the working segment 16, such as, for example, an epoxy or a UV-cured epoxy. A person of skill in the art will appreciate, however, that other methods of securing the shape-memory wire 42 at the distal end 30 of the working segment 16 can be used without departing from the scope of the disclosure. The distal end 28 of the flexible distal tip segment 20 may be plugged or sealed, for example using an adhesive, to prevent blood or other fluids from entering the distal end 28 of the flexible distal tip segment 20 during use. An adhesive, such as a UV-cured epoxy or other adhesive materials known in the art may be used to seal the distal end 28 of the flexible distal tip segment 20. The working segment 16 and the flexible distal tip segment 20 may optionally be entirely filled with an adhesive material. The working segment 16 can be formed in a variety of shapes, for example a generally circular or helical shape. One or more sensing and/or energy delivery elements may be formed on an outer surface of the working segment.

EXAMPLES

The following examples of a method of use and manufacture, respectively, are provided as additional disclosure although the specifics should be generally appreciated by those of skill in the art to which this disclosure pertains.

Method of Use Example

A method of diagnosing or treating cardiac tissue includes inserting an introducer into a patient and advancing the introducer to a location adjacent a tissue to be diagnosed or treated, providing an electrophysiology catheter comprising an elongated catheter body defining a lumen therethrough, the elongated catheter body having a proximal segment, a flexible distal tip segment having a pre-formed bend forming an angle of about 100 degrees to about 175 degrees, and a working segment having a distal end and a generally circular configuration in an unbiased state, wherein the working segment is positioned between the proximal segment and the flexible distal tip segment, a plurality of sensing and/or energy delivery elements disposed along an outer surface of the working segment and a shape-memory wire extending through the lumen of the catheter body and terminating at the distal end of the working segment, advancing the electrophysiology catheter through the introducer to expose the flexible distal tip segment, wherein the flexible distal tip segment exits a distal end of the introducer in a lateral direction relative to a longitudinal direction of the introducer body, further advancing the electrophysiology catheter to expose the working segment, wherein the working segment adopts the generally circular configuration after exiting the distal end of the introducer, placing the working segment against the tissue to be diagnosed or treated; and diagnosing or treating the tissue using the sensing and/or energy delivery elements.

Manufacturing Example 1

A method of manufacturing a catheter having an atraumatic distal tip includes extruding a catheter body, the catheter body having a proximal segment, the catheter body further defining a lumen therethrough, extruding a working segment and a flexible distal tip segment, inserting a shape-memory wire through the lumen to a distal end of the working segment, forming a bend in the flexible distal tip segment having an angle of between about 100 degrees to about 175 degrees, forming the working segment into a generally circular configuration, forming one or more sensing and/or energy delivery elements on the working segment, and affixing the working segment and the flexible distal tip segment to the catheter body.

Manufacturing Example 2

The method of example 1, further including the step of securing a distal end of the shape-memory wire at the distal end of the working segment.

Manufacturing Example 3

The method of example 2, wherein the step of securing a distal end of the shape-memory wire at the distal end of the working segment comprises embedding the distal end of the shape-memory wire in an adhesive.

Manufacturing Example 4

The method of example 3, wherein the adhesive is a UV-cured adhesive.

Manufacturing Example 5

The method of example 1, further comprising sealing a distal end of the flexible distal tip segment.

Manufacturing Example 6

The method of example 5, wherein the step of sealing a distal end of the flexible distal tip segment comprises filling the distal end of the flexible distal tip segment with an adhesive.

Manufacturing Example 7

The method of example 6, wherein the adhesive is a UV-cured adhesive.

Manufacturing Example 8

The method of example 1, wherein the step of forming one or more sensing and/or energy delivery elements comprises forming one or more of a radiofrequency electrode, an acoustic transducer, an optical element and a microwave element on the working segment.

Although several embodiments have been described above with a certain degree of particularity, those skilled in the art could make numerous alterations to the disclosed embodiments without departing from the scope of this disclosure. For example, while the flexible distal tip segments having a pre-formed bend have been described primarily with respect to catheters having a generally circular or helical working segment, flexible distal tip segments having a pre-formed bend may be incorporated into various types of catheters and other medical devices, including devices have curved or straight distal portions, without departing from the scope of the present disclosure.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present disclosure, and do not create limitations, particularly as to the position, orientation, or use of the various embodiments described and depicted herein. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the scope of the claimed invention.

What is claimed is:

1. A kit for the diagnosis or treatment of tissue in a body cavity, comprising: an introducer having an introducer body defining a lumen therethrough; and an electrophysiology catheter insertable through the lumen of the introducer body, the electrophysiology catheter comprising an elongated catheter body defining a lumen therethrough, the elongated catheter body having a proximal segment, a working segment located distally of the proximal segment, the working segment having a distal end and a generally circular configuration in an unbiased state, and a flexible distal tip segment adjacent the distal end of the working segment, the flexible distal tip segment having a proximal end and a distal end, the proximal end and the distal end being off-set from one another by an angle of between 100 degrees to 175 degrees via one of a bend pre-formed in the catheter body via thermosetting and a curve pre-formed in the catheter body via thermosetting; at least one of a cardiac sensing element and an energy delivery element disposed along an outer surface of the working segment; and a shape-memory wire extending through the lumen of the catheter body from the proximal segment and terminating at the distal end of the working segment, wherein the flexible distal tip segment retains its pre-formed bend or pre-formed curve when inserted through the lumen of the introducer, such that the flexible distal tip segment exits a distal end of the introducer in a lateral direction relative to a longitudinal direction of the introducer body.

2. The kit of claim 1, wherein the pre-formed bend forms an angle of 115 degrees to 125 degrees.

3. The kit of claim 1, wherein the flexible distal tip segment is less than 20 mm in length.

4. The kit of claim 1, wherein the flexible distal tip segment comprises a segment having a length dimension of 5 mm to 10 mm.

5. The kit of claim 1, wherein the at least one of a cardiac sensing element and an energy delivery element comprises a plurality of radiofrequency electrodes.

6. The kit of claim 1, wherein the at least one of a cardiac sensing element and an energy delivery element comprises a plurality of sensing elements and/or energy delivery elements, and wherein said energy delivery elements comprise at least one of a plurality of radiofrequency electrodes, a plurality of acoustic transducers, a plurality of optical elements and a plurality of microwave elements.

7. The kit of claim 1, wherein the flexible distal tip segment is fabricated of materials that are free of electrically conductive properties.

8. The kit of claim 1, wherein a distal end of the shape-memory wire is secured at the distal end of the working segment.

9. The kit of claim 8, wherein the distal end of the shape-memory wire is embedded in an adhesive.

10. The kit of claim 1, wherein the distal end of the flexible distal tip segment comprises one of a plug or a seal.

11. The kit of claim 10, wherein the plug or the seal comprises an adhesive.

12. The kit of claim 11, wherein the adhesive comprises a UV-cured adhesive.

13. The kit of claim 1, wherein the flexible distal tip segment comprises an intermediate section between the proximal end and the distal end, and further comprising a flowable adhesive material filling the distal end and the proximal end, and wherein the intermediate section comprises a substantially hollow section devoid of the flowable adhesive.

14. The kit of claim 1, wherein the working segment and the flexible distal tip segment are integrally-formed as a unitary polymeric piece.

15. The kit of claim 1, wherein the flexible distal tip segment and the working segment are formed separately and bonded together.

16. The kit of claim 1, wherein the pre-formed bend and the working segment curve in the same direction.

17. The kit of claim 1, wherein the catheter is a 3 French catheter.

18. An electrophysiology catheter having an atraumatic tip, comprising a body defining a lumen, the body comprising a generally straight proximal segment, a flexible distal tip segment having a bend pre-formed in the body via thermosetting and a working segment having a distal end and a generally circular configuration in an unbiased state, the working segment being located between the proximal segment and the flexible distal tip segment; at least one of a sensing element and an energy delivery element disposed along the working segment; and a shape-memory wire extending through the lumen and terminating at the distal end of the working segment, wherein the pre-formed bend forms an angle of between 100 degrees to 175 degrees, and wherein a length of the flexible distal tip segment comprises ⅙ the length of the working segment or less and wherein the pre-formed bend is not straightened when the electrophysiology catheter is inserted into an introducer.

19. The catheter of claim 18, wherein the pre-formed bend forms an angle of 115 degrees to 125 degrees.

20. The catheter of claim 18, wherein the length of the flexible distal tip segment is ¹⁄₁₀ the length of the working segment or less.

21. The catheter of claim 18, wherein a distal end of the shape-memory wire is secured at the distal end of the working segment.

22. The catheter of claim 21, wherein the distal end of the shape-memory wire is embedded in an adhesive.

23. The catheter of claim 18, wherein the flexible distal tip segment comprises a proximal end, a distal end and an intermediate section between the proximal end and the distal end, wherein the distal end and the proximal end are adhesive-filled, and wherein the intermediate section is substantially hollow.

24. The catheter of claim 18, wherein the at least one of the sensing element and the energy delivery element comprises a plurality of radiofrequency electrodes.

25. The catheter of claim 18, wherein the at least one of the sensing element and the energy delivery element comprises a plurality of at least one of a radiofrequency electrode, an acoustic transducer, an optical element and a microwave element.

* * * * *